US005940519A

United States Patent [19]

Kuo

[11] Patent Number: 5,940,519

[45] **Date of Patent: *Aug. 17, 1999**

[54] ACTIVE NOISE CONTROL SYSTEM AND METHOD FOR ON-LINE FEEDBACK PATH MODELING AND ON-LINE SECONDARY PATH MODELING

[75] Inventor: Sen M. Kuo, DeKalb, Ill.

[73] Assignee: Texas Instruments Incorporated, Dallas, Tex.

[ * ] Notice: This patent is subject to a terminal disclaimer.

[21] Appl. No.: 08/992,823

[22] Filed: Dec. 17, 1997

Related U.S. Application Data

[60] Provisional application No. 60/033,458, Dec. 17, 1996.

[51] Int. Cl.[6] .................. A61F 11/06

[52] U.S. Cl. .................. 381/71.11; 381/71.8; 381/71.1

[58] Field of Search .................. 381/71.11, 71.12, 381/71.8, 71.5, 71.4, 71.3, 71.1; 364/724.19, 724.2

[56] References Cited

U.S. PATENT DOCUMENTS

| | | | |
|---|---|---|---|
| 5,396,561 | 3/1995 | Popovich et al. | 381/71.11 |
| 5,502,869 | 4/1996 | Smith et al. | 381/71.9 |

*Primary Examiner*—Ping Lee
*Attorney, Agent, or Firm*—Robert D. Marshall, Jr.; Gerald E. Laws; Richard L. Donaldson

[57] ABSTRACT

A feedforward active noise control system (50) is provided that includes a reference sensor (16), a secondary source (18), an error sensor (20), and an active noise control system controller (10) for generating an anti-noise signal to attenuate a noise signal provided through a media. The feedforward active noise control system (50) performs on-line feedback path modeling and on-line secondary path modeling.

19 Claims, 2 Drawing Sheets

ACTIVE NOISE CONTROL SYSTEM AND METHOD FOR ON-LINE FEEDBACK PATH MODELING AND ON-LINE SECONDARY PATH MODELING

RELATED APPLICATIONS

This application claims priority under 35 USC 119(e) (1) of provisional application number 60/033,458 filed Dec. 17, 1996.

This application is related to the following co-pending U.S. patent applications: Ser. No. 08/992,699 entitled Off-Line Feedback Path Modeling Circuitry and Method for Off-Line Feedback Path Modeling, (TI Docket No. TI-24756); Ser. No. 08/991,726 entitled Active Noise Control System and Method for On-Line Feedback Path Modeling, (TI Docket No. TI-18587); Ser. No. 08/992,933 entitled Off-Line Path Modeling Circuitry and Method for Off-Line Feedback Path Modeling and Off-Line Secondary Path Modeling, (TI Docket No. TI-24757); and Ser. No. 08/992,777 entitled Digital Hearing Aid and Method for Active Noise Reduction, (TI Docket No. TI-18679), all filed concurrently on Dec. 17, 1996.

TECHNICAL FIELD OF THE INVENTION

This invention relates generally to the field of control systems and more particularly to an active noise control system and method for on-line feedback path modeling and on-line secondary path modeling.

BACKGROUND OF THE INVENTION

Active noise control systems are concerned with the reduction of any type of undesirable disturbance or noise signal provided by a noise source through an environment, whether it is borne by electrical, acoustic, vibration, or any other kind of noise media. Since the noise source and environment are often time-varying, the noise signal will often be non-stationary with respect to frequency content, amplitude, and velocity. Active noise control systems control noise by introducing a canceling "anti-noise" signal into the system environment or media through an appropriate secondary source. The anti-noise signal is ideally of equal amplitude and 180 degrees out of phase with the noise signal. Consequently, the combination of the anti-noise signal with the noise signal at an acoustical summing junction results in the cancellation or attenuation of both signals and hence a reduction in noise.

In order to produce a high degree of noise signal attenuation, the amplitude and phase of both the noise and anti-noise signals must match closely as described above. Generally, this is accomplished by an active noise control system using an active noise control system controller that performs digital signal processing using one or more adaptive algorithms for adaptive filtering. The adaptive filtering, and more specifically the adaptive algorithms, track all of the changes in the noise signal and the environment in real-time by minimizing an error signal and continuously tracking time variations of the environment. The adaptive filtering may use any of a variety of known and available adaptive algorithms, such as the least-mean-square ("LMS") algorithm, to establish the taps or coefficients of an associated adaptive filter that models the noise source and environment to reduce or minimize the error or residual signal.

Active noise control systems, as compared to passive noise control systems, provide potential benefits such as reduced size, weight, volume, and cost in addition to improvements in noise attenuation. Active noise control is an effective way to attenuate noise that is often difficult and expensive to control using passive means and has application to a wide variety of problems in manufacturing, industrial operations, and consumer products.

Active noise control systems may generally be divided into feedforward active noise control systems and feedback active noise control systems. The present invention will be illustrated as applied to a feedforward active noise control system and thus the present invention will be described in this context.

A feedforward active noise control system generally includes a reference sensor for sensing a noise signal from a noise source and generating a corresponding primary signal in response; an active noise control system controller for generating a secondary signal; a secondary source, located downstream from the reference sensor, for receiving the secondary signal and generating an anti-noise signal to cancel or attenuate the noise signal; and an error sensor for detecting a residual signal and generating a corresponding error signal in response. The residual signal is equivalent to the difference between the noise signal and the anti-noise signal as provided to the error signal through a primary environment. The active noise control system controller receives the primary signal and the error signal and generates the secondary signal in response.

The active noise control system controller is implemented using a digital signal processor and performs digital signal processing using a specific adaptive algorithm, depending on the type of cancellation scheme employed, for adaptive filtering. Also, the reference sensor, the secondary source, and the error sensor may include interface circuitry for interfacing with the active noise control system controller. The interface circuitry may include analog-to-digital converters, digital-to-analog converters, analog filters such as low pass filters and automatic gain control amplifiers so that signals can be exchanged in the correct domain, i.e., either the digital or analog domain. The interface circuitry may be provided separately.

Feedforward active noise control systems include a primary path that has a transfer function that may be denoted as $P(z)$. The primary path may be defined as the environment from the reference sensor to the error sensor. Feedforward active noise control systems also include a secondary path and a feedback path. The secondary path has a transfer function that may be denoted as $S(z)$. The secondary path may be defined as the environment from the output of the active noise control system controller to the output of the error sensor. This may include interface circuitry such as a digital-to-analog converter, an analog filter, a power amplifier, a loud speaker, an error microphone, and other devices. The feedback path also has a transfer function and may be denoted by $F(z)$. The feedback path may be defined as the environment from the output of the active noise control system controller to the output of the reference sensor. The active noise control system controller, using a digital signal processor, may include an adaptive filter, that is normally denoted by $W(z)$, that attempts to adaptively model the primary path and inversely model the secondary path. The objective of the adaptive filter $W(z)$ is to minimize the residual signal or error signal. The adaptive filtering performed by adaptive filter $W(z)$ may be performed either on-line or off-line.

Feedforward active noise control systems suffer from a serious drawback that often harms overall system performance. Whenever the secondary source generates an anti-noise signal to cancel the noise signal, a portion of the anti-noise signal radiates upstream to the reference sensor where it is received along with the noise signal. The path that the anti-noise signal takes when traveling from the secondary source to the reference sensor is the feedback path. The feedback path, once again, may be defined as the media environment from the output of the active noise control system controller to the output of the reference sensor. The portion of the anti-noise signal flowing to the reference sensor along the feedback path is part of a feedback signal that travels through the feedback path. As a consequence of the feedback signal being received at the reference sensor, an incorrect primary signal is provided to the active noise control system controller by the reference sensor and, hence, overall system performance is harmed. If the feedback signal is in phase with the noise signal, the reference sensor will generate a primary signal that is too large. If the feedback signal is out of phase with the noise signal, the reference senor will also generate a signal that is incorrect. In any event, the feedback signal is undesirable and harms overall performance. The feedback signal may also allow the introduction of poles into the response of the system transfer function which results in potential instability if the gain of the feedback loop becomes large.

In certain applications, overall system performance is significantly degraded if the effects of the feedback path are not modeled and neutralized. The modeling of the feedback path and neutralization of the feedback signal becomes especially critical to overall active noise control system performance in applications in which the secondary source is in close proximity or in close communication with the reference sensor. Such systems would include, for example, appliances such as refrigerators and window air conditioner units in which the air ducts are relatively short. In such applications, the secondary source must be located close to the reference sensor by necessity and hence the feedback signal and its adverse effects will be greater.

The feedback path problem has been recognized in the past and several solutions have been proposed with limited success. A first set of proposed solutions has focused on the use, type, and placement of the reference sensors and the secondary sources, while a second set of proposed solutions has focused on signal processing techniques. The first set of proposed solutions involves the use and placement of directional reference sensors and secondary sources to limit or minimize the feedback signal. These proposed solutions add additional expense and complexity to the system and decrease overall reliability while making it difficult, if not impossible, to obtain good directivity over a broad range of frequencies.

The second set of proposed solutions has focused on signal processing techniques and has achieved limited success. The proposed solutions involving signal processing techniques may be generally separated into off-line modeling techniques and on-line modeling techniques. Both off-line modeling and on-line modeling are system identification techniques in which a signal is provided to the system and the resulting signal is analyzed to construct a model of the unknown system. This is accomplished by exciting an unknown path or environment with the known signal and then measuring or analyzing the resulting signal that is provided in response.

Off-line feedback path modeling techniques involve providing a known signal in the absence of the noise signal cancellation that is normally provided by the active noise control system. An adaptive algorithm is used to calculate the coefficients or taps of an adaptive filter to minimize the effects of the feedback path. Once the coefficients or taps are established off-line, during actual active noise control system operation, the taps or coefficients are fixed in a digital filter and are not changed during actual operation. Although off-line feedback path modeling techniques are adequate in certain situations, off-line modeling may not provide adequate performance when used in a system in which parameters are frequently changing. For example, parameters such as temperature and signal flow rate may frequently change resulting in an inaccurate feedback path model because of the changes.

Another problem with off-line feedback path modeling is that the noise signal must be eliminated or stopped for the off-line feedback path modeling to correctly model the unknown environment. This is often not practical in many real-world systems. For example, a power transformer that is energized and used to provide power to customers cannot be easily taken out of service so that off-line modeling may take place. In a system that changes frequently, it may be necessary to routinely perform off-line feedback path modeling so that the feedback path remains accurately modeled. In the event that a noise source cannot be shut off, off-line modeling may proceed if the known signal or modeling signal is provided at a very high amplitude for an extended period of time. In spite of this, the off-line model may still be inaccurate.

On-line feedback path modeling refers to the modeling of the feedback path while the noise signal is being provided to the unknown environment and the active noise control system is operating to cancel the noise signal. Ideally, on-line feedback modeling allows for any changes in the plant environment to be modeled while the active noise control system is operating and thus avoiding the problems encountered with off-line feedback path modeling when the environment or plant changes due to such things as temperature and flow changes. Unfortunately, prior attempts at providing on-line feedback path modeling have proven unsatisfactory and have failed to provide an on-line model of the feedback path.

One such technique focused on providing an adaptive neutralization filter in parallel with the feedback path. The adaptive neutralization filter approach, such as that described in U.S. Pat. No. 4,473,906 entitled "Active Acoustic Attenuator," may only effectively operate in an off-line feedback path modeling mode because of the fact that the adaptive neutralization filter will attempt to adapt even when the noise signal and the anti-noise signal are perfectly canceled. The feedback neutralization technique attempts to model the feedback path in such a way as to remove all portions of the primary signal that are correlated with the output of the adaptive filter, which, ideally, results in a system that appears to be without feedback. Since the primary noise signal is highly correlated with the anti-noise signal, the adaptive feedback neutralization filter will continue adapt even when the feedback signal is perfectly canceled. As a consequence, the adaptation of the feedback neutralization filter must be deactivated when the system is on-line. Also, when the noise signal contains narrowband frequency components, the adaptive feedback neutralization filter may fail to properly converge when attempting to adapt on-line.

Another proposed on-line feedback path modeling solution involves the use of an infinite-impulse response ("IIR") filter to compensate for the feedback signal. This approach has achieved only limited success. For example, in U.S. Pat. No. 4,677,677 entitled "Active Sound Attenuation System with On-Line Adaptive Feedback Cancellation," an adaptive IIR filter structure was proposed for use in an active noise control system. In this approach, the feedback path is considered part of the overall plant model but does not truly model the feedback path. This approach suffers several disadvantages which are inherent in adaptive IIR filters. For example, IIR filters are not unconditionally stable because of the possibility that some poles of the IIR filter will move outside of the unit circle during the adaptive process, resulting in instability. Also, due to the presence of local minima the adaptation may converge at one of the local minima. Furthermore, adaptive algorithms used with IIR filters often have a relatively slow convergence rate in comparison with that of FIR filters.

Other proposed on-line feedback path modeling solutions involve the use of a modeling signal that must be provided at a very high amplitude so that it may be distinguished from the noise signal. This solution introduce additional noise into the system that adversely affects overall active noise control system operation and performance.

In addition to the feedback path problem, feedforward active noise control systems also suffer from another serious drawback that also harms overall system performance. As mentioned previously, feedforward active noise control systems also include a secondary path, S(z), that is defined as the environment from the output of the active noise control system controller to the output of the error sensor. As mentioned previously, the secondary path will include interface circuitry and other devices that introduce additional transfer functions into the system which affect overall system operation. The presence of the secondary path transfer function S(z) may result in an unstable system that cannot or will not properly converge. The secondary path, just like the feedback path, is dependent upon environment conditions and is influenced by such parameters as temperature, flow, and other factors. Attempts at solving the secondary path problem have focused on signal processing techniques and have achieved limited success, similar to what was previously mentioned with respect to the feedback path problem.

SUMMARY OF THE INVENTION

From the foregoing it may be appreciated that a need has arisen for an active noise control system and method for on-line feedback path modeling and on-line secondary path modeling that eliminate or reduce the problems described above. In accordance with the present invention, an active noise control system and method for on-line feedback path modeling and on-line secondary path modeling are provided that provide a signal processing solution to the feedback signal problem by providing on-line modeling of the feedback path and neutralizing its effects so that an active noise control system will operate more efficiently and accurately. This is accomplished on-line, even while the feedback path and secondary path are changing and active noise cancellation is being performed. The present invention attenuates both broadband noise signals and narrowband noise signals.

According to an embodiment of the present invention, an active noise control system is provided for generating an anti-noise signal to attenuate a noise signal provided through a media. The active noise control system performs on-line feedback path modeling and on-line secondary path modeling and includes a reference sensor, a secondary source, an error sensor, and an active noise control system controller. The reference sensor receives the noise signal and a feedback signal and generates a primary signal in response. The secondary source receives a secondary signal and generates a corresponding anti-noise signal. The error sensor receives a residual signal and generates an error signal. The active noise control system controller receives the primary signal and the error signal and generates the secondary signal and performs on-line feedback path modeling and on-line secondary path modeling.

The present invention provides various technical advantages. A technical advantage of the present invention includes the ability to accurately perform on-line feedback path modeling and on-line secondary path modeling to account for any changes in either of these paths so that overall system performance and noise cancellation is enhanced. Still another technical advantage of the present invention includes the ability to implement the present invention using existing digital signal processing techniques and algorithms. Yet another technical advantage of the present invention includes increased active noise control system stability due to the elimination of the adverse feedback path and secondary path effects. Still another technical advantage of the present invention includes the ability to cancel or attenuate both broadband and narrowband noise signals. Still yet another technical advantage of the present invention includes the ability to accurately and simultaneously perform feedback path modeling and secondary path modeling without having to shut-off the noise signal. Other technical advantages are readily apparent to one skilled in the art from the following FIGUREs, description, and claims.

BRIEF DESCRIPTION OF THE DRAWINGS

For a more complete understanding of the present invention and the advantages thereof, reference is now made to the following brief description, taken in connection with the accompanying drawings and detailed description, wherein like reference numerals represent like parts, in which.

DETAILED DESCRIPTION OF THE INVENTION

Figure 1:
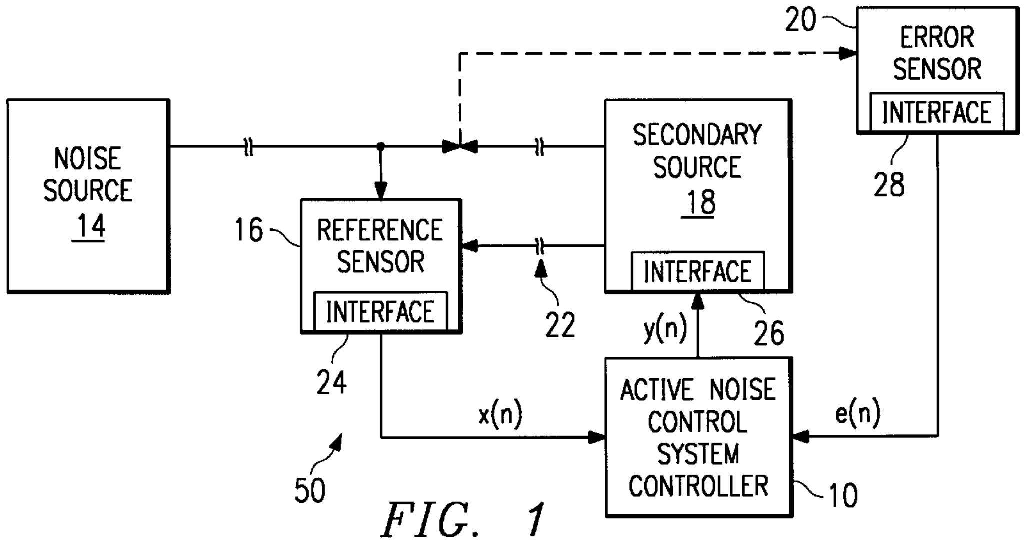
FIG. 1 is a block diagram illustrating a feedforward active noise control system according to the teachings of the present invention.

FIG. 1 is a block diagram of a feedforward active noise control system 50. Feedforward active noise control system 50 includes a noise source 14, a reference sensor 16, an active noise control system controller 10, a secondary source 18, and an error sensor 20. Noise source 14 generates or provides a noise signal through a plant environment where the signal may be received by reference sensor 16. The noise signal is shown flowing from noise source 14 in FIG. 1.

Reference sensor 16 generates a corresponding electronic signal x(n) which may be referred to as a primary signal x(n). Reference sensor 16 may be implemented using virtually any type of sensor such as a microphone, a tachometer, an accelerometer, an optical sensor, to name a few. Reference sensor 16 may also contain an interface circuitry 24 so that the noise signal may be received as an analog signal and the corresponding primary signal x(n) may be generated as a digital signal. Interface circuitry 24 may include any of a variety of devices such as an analog-to-digital converter, an analog filter, an amplifier controlled by an automatic gain control circuit, and any of a variety of other circuitry such as antialiasing circuitry.

Active noise control system controller 10 receives the primary signal x(n) and generates a corresponding electrical signal y(n), which may be referred to as a secondary signal y(n). The secondary signal y(n) is provided to secondary source 18 where it is received and provided back to the plant environment as an analog signal. The output signal of secondary source 18 may be referred to as an anti-noise signal and is designed to reduce, cancel, or neutralize the noise signal provided by noise source 14. Secondary source 18 may be implemented using virtually any signal source such as a speaker, a shaker, or virtually any other available signal source. Secondary source 18 may also include an interface circuitry 26 that allows the secondary signal y(n) to be converted from the digital domain to the analog domain and to be provided at a desired amplitude. Interface circuitry 26 may, for example, include any of variety of circuitry such as a digital-to-analog converter, analog filters, such as a low pass filter, and an amplifier controlled by an automatic gain control circuit.

As a consequence of introducing the anti-noise signal into the plant environment, a portion of the anti-noise signal also travels back to reference sensor 16 along a feedback path that is defined as the path from the output of active noise control system controller 10 to the output of reference sensor 16. A feedback signal 22 is shown flowing through the feedback path and includes, as one of its components, the portion of the anti-noise signal that is provided along the feedback path and may be referred to as an anti-noise feedback component. Feedback signal 22 also includes a modified modeling feedback component that is provided as part of the present invention. The modified modeling feedback component of feedback signal 22 is generated as a result of a modeling signal, that is provided as part of secondary signal y(n) and is discussed more fully below, flowing through the feedback path. Thus, feedback signal 22 includes an anti-noise feedback component and a modified modeling feedback component. Reference sensor 16 receives feedback signal 22 along with the noise signal and generates the primary signal x(n) as a result. Primary signal x(n) will then include a noise signal component and a feedback signal component with the feedback signal component including an anti-noise feedback component and a modified modeling feedback component. The introduction of feedback signal 22 to the input of reference sensor 16 results in the generation of an incorrect primary signal x(n). This will be discussed more fully below.

Error sensor 20 receives a residual signal that is the result of the combination of the noise signal and the anti-noise signal at an acoustical summing junction. The residual signal is ideally zero. The residual signal is zero when the anti-noise signal is provided at the acoustical summing junction at an amplitude equivalent to the noise signal but 180 degrees out of phase with the noise signal and entirely cancels the noise signal at the acoustical summing junction.

Error sensor 20 receives the residual signal and generates a corresponding error signal e(n). Error sensor 20 may be implemented using virtually any sensor. For example, error sensor 20, just as with reference sensor 16, may be implemented using a microphone, a tachometer, an accelerometer, an optical sensor, or virtually any other available sensor. Error signal e(n) may be provided in the digital domain through the use of an interface circuitry 28. Interface circuitry 28 may be similar to interface circuitry 24 and may include such circuitry as an analog-to-digital converter, a smoothing filter, and an amplifier controlled by an automatic gain control circuit. Error signal e(n) is provided to active noise control system controller 10 where it is received and used by a system and secondary path adaptive filter circuitry 66 to provide active noise control so that the generation of the secondary signal y(n) may be adjusted to improve the overall performance of feedforward active noise control system 50. System and secondary path adaptive filter circuitry 66 includes the main filter of active noise control system controller 10 and is illustrated more fully in FIG. 4 and described more fully below. Active noise control system controller 10 also performs on-line feedback path modeling, feedback path neutralization, on-line secondary path modeling, and secondary path compensation to reduce the effects of the feedback path and the secondary path.

Interface circuitry 24, interface circuitry 26, and interface circuitry 28 are illustrated in FIG. 1 as being provided as part of their respective sensor or source. However, it should be understood that the interface circuitry may be provided as discrete circuitry components provided independently or separately. The present invention is in no way limited by any one particular type of interface circuitry.

The existence of the secondary path, which is defined as the environment from the output of active noise control system controller 10 to the output of error sensor 20, introduces unknown, and often changing, effects that, if unaccounted for, will cause an error in the generation of error signal e(n). The error in the generation of error signal e(n) will ultimately harm overall system performance. The secondary path includes interface circuitry 26, secondary source 18, error sensor 20, and interface circuitry 28. The existence of these devices will affect the generation of error signal e(n) . The error signal e(n) will also include a modified modeling secondary path component that is provided as part of the present invention. The modified modeling secondary path component of error signal e(n) is generated as a result of a modeling signal v(n) being provided through the secondary path. The modeling signal v(n) is provided as part of secondary signal y(n) and is discussed more fully below. Active noise control system controller 10 receives error signal e(n) which includes the modified modeling secondary path component.

Figure 3:
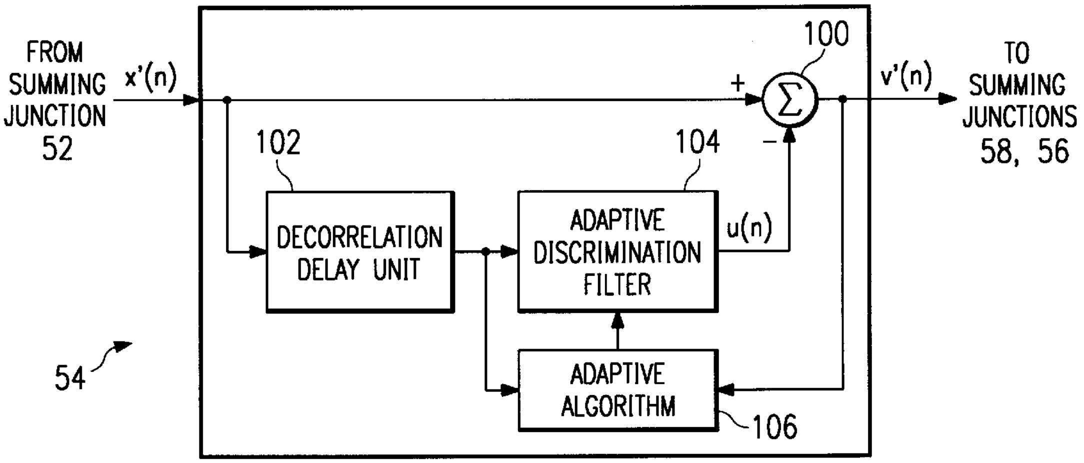
FIG. 3 is a block diagram illustrating a signal discrimination circuitry that may be used in the active noise control system controller in performing on-line feedback path modeling and on-line secondary path modeling.
Figure 2:
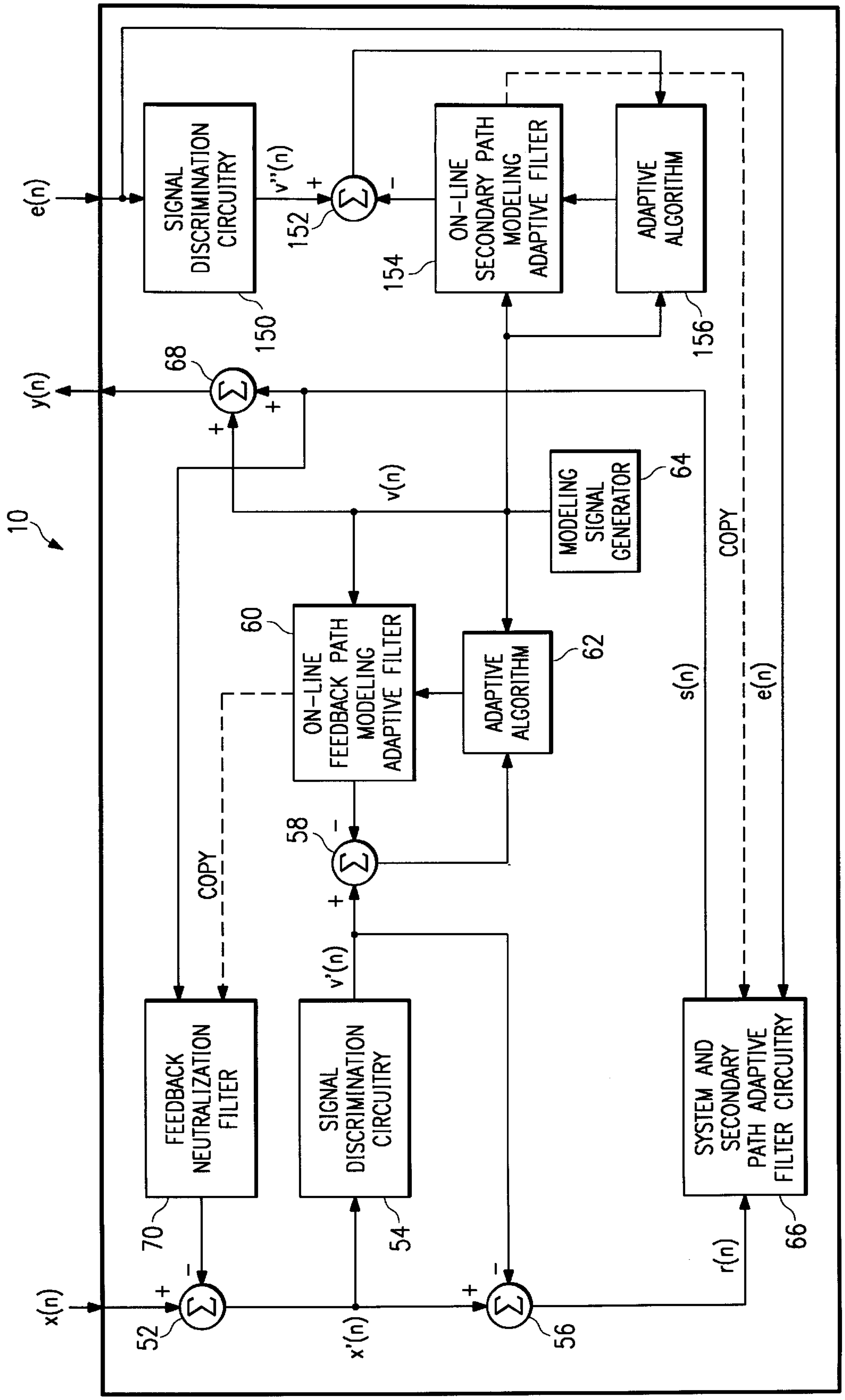
FIG. 2 is a block diagram illustrating an active noise control system controller of the feedforward active noise control system.

Active noise control system controller 10, illustrated more fully in FIGS. 2 and 3, receives primary signal x(n) and error signal e(n) and generates secondary signal y(n) in response. Active noise control system controller 10 includes on-line feedback path modeling circuitry, on-line secondary path modeling circuitry, feedback signal neutralization circuitry, and secondary path compensation circuitry. The feedback path may be modeled by a transfer function denoted by F(z) while the secondary path may be modeled by a transfer function denoted by S(z). Active noise control system controller 10 also includes system and secondary path adaptive filter circuitry 66, which includes the main system filter, for adaptively modeling the primary plant or environment which has a transfer function denoted by P(z).

Active noise control system controller 10 also includes a modeling signal generator 64 that is used to introduce a modeling signal into feedforward active noise control system 50 so that the modified modeling feedback component and the modified modeling secondary path component may be generated as a result of the modeling signal v(n) having passed through the feedback path and the secondary path, respectively. The modified modeling feedback component becomes correlated to the feedback path as a result of the modeling signal v(n) having passed through the feedback path. The modified modeling secondary path component becomes correlated to the secondary path as a result of the modeling signal v(n) having passed through the secondary path. The modeling signal v(n) is normally provided at an amplitude that is significantly smaller than the primary signal x(n) and secondary signal y(n). The modified modeling signal v(n) is used in conjunction with active noise control system controller 10 to provide on-line feedback path modeling and on-line secondary path modeling. Active noise control system controller 10 controls feedforward active noise control system 50 by reducing or minimizing the error signal e(n) while also performing on-line feedback path modeling and on-line secondary path modeling which enhances overall system performance and noise canceling capability.

Active noise control system controller 10 may be implemented using digital circuitry such as application specific integrated circuitry or digital circuitry such as a digital signal processor. For example, Texas Instruments Incorporated provides a family of digital signal processors including the TMS320C25 and the TMS320C30 digital signal processors. The advent of high-speed digital signal processors and related hardware have made the implementation of the present invention more practical. Many digital signal processors are implemented using a fixed-point data format. In such a case, automatic gain control circuitry must be used at each data input to extend the analog-to-digital converter dynamic range of interface circuitry 24 and interface circuitry 28.

FIG. 2 is a block diagram of active noise control system controller 10 and includes various circuitry for performing on-line feedback path modeling and associated feedback signal neutralization circuitry, and on-line secondary path modeling circuitry and associated secondary path compensation circuitry. Active noise control system controller 10 receives the primary signal x(n) from reference sensor 16 and the error signal e(n) from error sensor 20 and performs various filtering, processing, and modeling functions to generate secondary signal y(n), which is then provided to secondary source 18. Primary signal x(n) is received at a summing junction 52 along with the output signal of a feedback neutralization filter 70. Summing junction 52 subtracts the output signal of feedback neutralization filter 70 from primary signal x(n) to generate an output signal x'(n) in response. The signal x'(n) may be referred to as a feedback neutralized primary signal since the anti-noise feedback component of feedback signal 22, which is provided as a component of primary signal x(n), is removed by feedback neutralization filter 70.

Signal discrimination circuitry 54 receives the feedback neutralized primary signal x'(n) and generates an output signal v'(n), which may be referred to as a modified modeling feedback signal v'(n) because the noise signal component has been removed from feedback neutralized primary signal x'(n) Modified modeling feedback signal v'(n) represents a modeling signal v(n) after having passed through the feedback path. The feedback path, once again, is defined as the plant environment from the output of active noise control system controller 10 to the output of reference sensor 16.

Signal discrimination circuitry 54, in effect, extracts the modified modeling feedback component that is included as a component of feedback neutralized primary signal x'(n). This is accomplished in spite of the fact that the magnitude of modeling signal v(n) will generally be significantly less than the magnitude of the noise signal. Signal discrimination circuitry 54 uses a decorrelation delay unit and a digital adaptive filter to generate a predicted noise signal u(n) that does not include any component of feedback signal 22. Predicted noise signal u(n) may then be subtracted from feedback neutralized primary signal x'(n) to generate the modified modeling feedback signal v'(n). Signal discrimination circuitry 54 is illustrated more fully in FIG. 3.

Feedback neutralized primary signal x'(n) is also provided to a summing junction 56 along with modified modeling feedback signal v'(n). Summing junction 56 subtracts modified modeling feedback signal v'(n) from feedback neutralized primary signal x'(n) to generate an output signal r(n) which may be referred to as a processed primary signal. Processed primary signal r(n) will contain the noise signal component of primary signal x(n) after the modified modeling feedback component of feedback signal 22 has been removed from feedback neutralized primary signal x'(n). Processed primary signal r(n) is then provided to system and secondary path adaptive filter circuitry 66 for further processing.

System and secondary path adaptive filter circuitry 66 functions to generate an output signal s(n) which may be referred to as a generated secondary signal. An adaptive active noise control filter 200 and a secondary path compensation filter 202, both shown in FIG. 4, receive processed primary signal r(n), and an adaptive algorithm 204, also shown in FIG. 4, receives a secondary path compensated primary signal and the error signal e(n) so that generated secondary signal s(n) may be generated. Adaptive algorithm 204 generates coefficients or taps that may be used by system and secondary path adaptive filter circuitry 66 to generate output signal s(n) at an appropriate value to cancel the noise signal. Adaptive algorithm 204 generates the taps or coefficients that will minimize the value of error signal e(n).

Modeling signal generator 64 is also provided to generate a white-noise, random signal, or chirp signal which may be referred to as a modeling signal v(n). Modeling signal generator 64 may use any technique to generate a white-noise signal, a random signal, a chirp signal, or virtually any signal capable of serving as a modeling signal to excite an environment or path. However, modeling signal generator 64 will generally use one of two basic techniques that can be implemented for random number or chirp signal generation. The first technique uses a lookup table method using a set of stored samples. The second technique uses a signal generation algorithm. Both techniques obtain a sequence that repeats itself after a finite period, and therefore may not be truly random for all time.

Modeling signal v(n) is provided to a summing junction 68 along with generated secondary signal s(n). As previously mentioned, modeling signal v(n) is generally provided at an amplitude that is much smaller than either the noise signal or anti-noise signal to reduce the modeling signal's effects on feedforward active noise control system 50. Summing junction 68 sums these two signals and generates the secondary signal y(n) as its output. Thus, secondary signal y(n) will include two components: (1) modeling signal v(n); and (2) generated secondary signal s(n).

An on-line feedback path modeling adaptive filter 60 and a corresponding adaptive algorithm 62 are also provided as part of active noise control system controller 10. On-line feedback path modeling adaptive filter 60 and adaptive algorithm 62 are used to model the feedback path and periodically provide filter coefficient or tap settings to feedback neutralization filter 70. The feedback path, once again, being defined as the plant environment from the output of the active noise control system controller 10 to the output of reference sensor 16. On-line feedback path modeling adaptive filter 60 provides filter tap settings to feedback neutralization filter 70 every fixed number of sample periods. The fixed number of sample periods may be a programmable value and may occur every sample period or, preferably, at every fixed number of sample periods to provide acceptable overall system performance. For example, the fixed number of sample periods may occur every 20 sample periods and will generally be dependent on how frequently the feedback path changes. The sample period is inversely related to the sampling rate, which must be high enough to satisfy the Nyquist criterion such that the sampling rate must be greater than or equal to two times the highest frequency of interest. Also, the real-time digital signal processing performed by active noise control system controller 10, which includes on-line feedback path modeling adaptive filter 60, must be performed at a sample period that is less than the sampling period of feedforward active noise control system 50.

On-line feedback path modeling adaptive filter 60 and adaptive algorithm 62 receive modeling signal v(n) as an input. Adaptive algorithm 62 also receives the output signal of a summing junction 58 as an input which is equivalent to the difference between modified modeling feedback signal v'(n) and the output signal of on-line feedback path modeling adaptive filter 60. The function of adaptive algorithm 62 is to adjust the taps or coefficients of on-line feedback path modeling adaptive filter 60 to minimize the mean-square value of the output signal provided by summing junction 58. The output signal of summing junction 58 may be thought of as an error signal, such as a feedback path modeling error signal, to be minimized. Therefore, the filter coefficient or taps are updated so that the error signal is progressively minimized on a sample-by-sample basis. On-line feedback path modeling adaptive filter 60 and adaptive algorithm 62 may be implemented as any digital adaptive filter and adaptive algorithm such as those described below with reference to adaptive noise control system filter 66, adaptive active noise control filter 200, and adaptive algorithm 204. On-line feedback path modeling adaptive filter 60 and adaptive algorithm 62 provide an on-line feedback path model.

Feedback neutralization filter 70 is a non-adaptive digital filter and receives the tap or coefficient settings from on-line feedback path modeling adaptive filter 60. As mentioned above, these coefficients may be copied from on-line feedback path modeling adaptive filters 60 to feedback neutralization filter 70 every sample period or preferably, at selected intervals. Feedback neutralization filter 70 receives the tap or coefficient information and processes its input signal, secondary signal s(n), in response. Feedback neutralization filter 70 filters this signal to generate an output signal that is about equivalent to the anti-noise feedback component of feedback signal 22, which is provided through the feedback path. The output signal of feedback neutralization filter 70 is then provided to summing junction 52 where the anti-noise feedback component of feedback signal 22 is removed from primary signal x(n).

A signal discrimination circuitry 150 receives error signal e(n) from error sensor 20 and generates an output signal v"(n), which may be referred to as a modified modeling secondary path signal v"(n). Modified modeling secondary path signal v"(n) represents a modeling signal v(n) after having passed through the secondary path. The secondary path, once again, is defined as the environment from the output of active noise control system controller 10 to the output of error sensor 20.

Signal discrimination circuitry 150, in effect, extracts the modified modeling secondary path component that is included as a component of the error signal e(n). This is accomplished in spite of the fact that the magnitude of modeling signal v(n) will generally be significantly less than the magnitude of the noise signal or anti-noise signal. Signal discrimination circuitry 150 uses a decorrelation delay unit and a digital adaptive filter to generate a predicted noise signal u(n) that does not include any component of modified modeling signal v(n) or the modified modeling secondary path component of the error signal e(n). Predicted noise signal u(n) may then be subtracted from error signal e(n) to generate the modified modeling secondary path signal v'(n). Signal discrimination circuitry 150 may be implemented similarly to signal discrimination circuitry 54 which is illustrated more fully in FIG. 3.

An on-line secondary path modeling adaptive filter 154 and a corresponding adaptive algorithm 156 are also provided as part of active noise control system controller 10. On-line secondary path modeling adaptive filter 154 and adaptive algorithm 156 are used to model the secondary path and to periodically provide filter coefficient or tap settings to secondary path compensation filter 202 of system and secondary path adaptive filter circuitry 66, both of which are illustrated more fully in FIG. 4. The secondary path, once again, is defined as the environment from the output of active noise control system controller 10 to the output of error sensor 20. On-line secondary path modeling adaptive filter 154 provides filter tap settings to secondary path compensation filter 202 every fixed number of sample periods. The fixed number of sample periods may be a programmable value and may occur every sample period or, preferably, at every fixed number of sample periods to provide acceptable overall system performance. For example, the fixed number of sample periods may occur every 20 sample periods and will generally be dependent on how frequently the secondary path changes. Also, the real-time digital signal processing performed by active noise control system controller 10, which includes on-line secondary path modeling adaptive filter 154, must be performed at a sample period that is less than the sampling period of feedforward active noise control system 50.

On-line secondary path modeling adaptive filter 154 and adaptive algorithm 156 receive modeling signal v(n) as an input. Adaptive algorithm 156 also receives the output signal of a summing junction 152 as an input which is equivalent to the difference between modified modeling secondary path signal v"(n) and the output signal of on-line secondary path modeling adaptive filter 154. The function of adaptive algorithm 156 is to adjust the taps or coefficients of on-line secondary path modeling adaptive filter 154 to minimize the mean-square value of the output signal provided by summing junction 152. The output signal of summing junction 152 may be thought of as an error signal, such as a secondary path modeling error signal, to be minimized. Therefore, the filter coefficient or taps are updated so that the error signal is progressively minimized on a sample-by-sample basis. On-line secondary path modeling adaptive filter 154 and adaptive algorithm 156 may be implemented as any digital adaptive filter and adaptive algorithm such as those described below with reference to adaptive noise control system filter 66, adaptive active noise control filter 200, and adaptive algorithm 204. On-line secondary path modeling adaptive filter 154 and adaptive algorithm 156 provide an on-line secondary path model.

Figure 4:
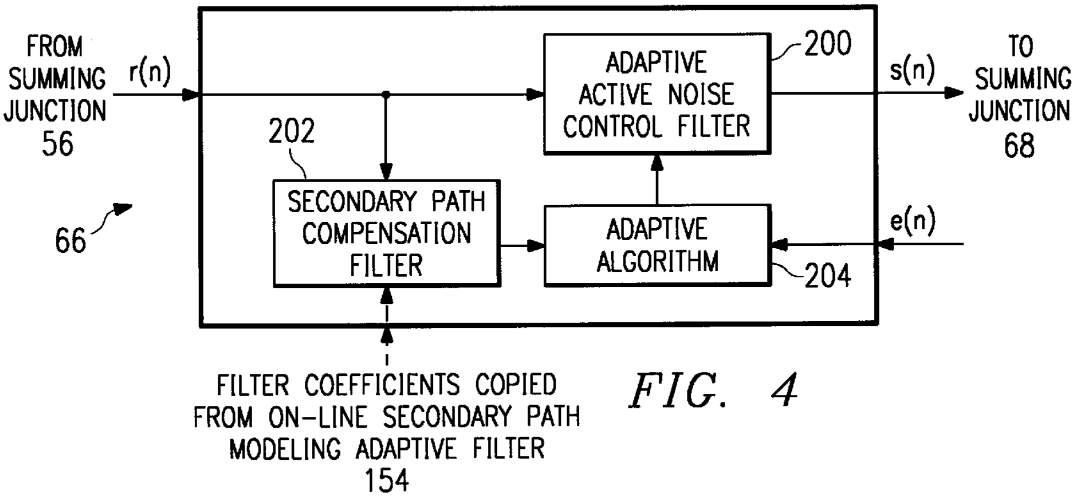
FIG. 4 is a block diagram illustrating a system and secondary path adaptive filter circuitry of the active noise control system controller.

Secondary path compensation filter 202, illustrated more fully in FIG. 4, is a non-adaptive digital filter and receives the tap or coefficient settings from on-line secondary path modeling adaptive filter 154. As mentioned above, these coefficients may be copied from on-line secondary path modeling adaptive filter 154 to secondary path compensation filter 202 every sample period or preferably, at selected intervals. Secondary path compensation filter 202 receives the tap or coefficient information and processes its input signal, processed primary signal r(n), in response. Secondary path compensation filter 202 filters this signal to generate a secondary path compensated primary signal that is provided to adaptive algorithm 204.

In operation, active noise control system controller 10 receives primary signal x(n) from reference sensor 16 along with error signal e(n) from error sensor 20 as input signals. The primary signal x(n) may be thought of as containing a noise signal component and a feedback signal 22 component. Once again, feedback signal 22 component includes at least two components, the anti-noise feedback component, and the modified modeling feedback component. The error signal e(n) includes the modified modeling secondary path component. The primary signal x(n) passes through summing junction 52 where the anti-noise feedback component of feedback signal 22 is removed by feedback neutralized filter 70 to generate feedback neutralized primary signal x'(n) Feedback neutralized primary signal x'(n) is provided to signal discrimination circuitry 54 and summing junction 56.

Signal discrimination circuitry 54 receives feedback neutralized primary signal x'(n) and generates modified modeling feedback signal v'(n) in response. Modified modeling feedback signal v'(n) is also provided as an input to summing junction 56. Summing junction 56 subtracts the modified modeling feedback signal v'(n) from feedback neutralized primary signal x'(n) to remove the modified modeling feedback component of x'(n) and to generate processed primary signal r(n). Processed primary signal r(n) is received at system and secondary path adaptive filter circuitry 66 where it is received by secondary path compensation filter 202 and adaptive active noise control filter 200. Adaptive algorithm 204 receives the error signal e(n) from error sensor 20 and the secondary path compensated primary signal from secondary path compensation filter 202. Adaptive algorithm 204 adjusts or calculates the coefficients or taps of adaptive active noise control filter 200 to minimize error signal e(n). As a result, the generated secondary signal s(n) is provided as an output of system and secondary path adaptive filter circuitry 66. Ideally, the generated secondary signal s(n) is about equal to a signal that is 180 degrees out of phase with the noise signal so that the noise signal will be canceled when combined with the generated secondary signal s(n) after it is converted to the analog domain by secondary source 18.

Alternatively, summing junction 56 is not provided and the feedback neutralized primary signal x'(n) serves as processed primary signal r(n). In such a case, feedback neutralized primary signal x'(n) functions as processed primary signal r(n) except that processed primary signal r(n) will include the modified modeling feedback component, or modified modeling feedback signal v'(n), as a component. This may be accomplished because of the fact that the average amplitude of the modified modeling feedback signal v'(n) will generally be significantly less than that of the noise signal component of the primary signal x(n). The noise signal component is also included as a component of feedback neutralized primary signal x'(n).

Meanwhile, modeling signal generator 64 provides modeling signal v(n) to summing junction 68, on-line feedback path modeling adaptive filter 60, adaptive algorithm 62, on-line secondary path modeling adaptive filter 154, and adaptive algorithm 156. The modeling signal v(n) is combined with the generated secondary signal s(n) at summing junction 68 to generate the secondary signal y(n). The secondary signal y(n) is then provided to secondary source 18 so that a corresponding anti-noise signal may be generated to cancel the noise signal. The amplitude of the modeling system v(n) will, preferably, be somewhat smaller than the noise signal. This is to allow the modeling signal to excite the feedback path without unduly or significantly affecting the overall plant environment.

On-line feedback path modeling adaptive filter 60 and adaptive algorithm 62 receive modeling signal v(n) and work together to model the feedback path. In doing this, the appropriate taps or coefficients of feedback neutralization filter 70 are calculated by adaptive algorithm 62 and provided to feedback neutralization filter 70 at selected intervals. As mentioned previously, these may be provided, each sample period or at selected intervals. The output of feedback neutralization filter 70 is then provided to summing junction 52 where the anti-noise feedback component of feedback signal 22 is removed from primary signal x(n).

Signal discrimination circuitry 150 receives the error signal e(n) and generates the modified modeling secondary path signal v"(n) in response. The modified modeling secondary path signal v"(n) is also provided as an input to summing junction 152 where the output of on-line secondary path modeling adaptive filter 154 is subtracted and the result is provided as an input to adaptive algorithm 156. On-line secondary path modeling adaptive filter 154 and adaptive algorithm 156 receive the modeling signal v(n) and work together to model the secondary path. In doing this, the appropriate taps or coefficients of secondary path compensation filter 202 are calculated by adaptive algorithm 156 and provided to secondary path compensation filter 202 at selected intervals. As mentioned previously, these may be provided, each sample period or at selected intervals.

As was mentioned previously, the error signal e(n) is provided to adaptive algorithm 204 of system and secondary path adaptive filter circuitry 66. Alternatively, a summing junction, not shown in FIG. 2, may be provided that subtracts the modified modeling secondary path component from the error signal e(n) before it is provided to adaptive algorithm 204. This normally is not required because of the fact that the average amplitude of the error signal e(n) will generally be significantly greater than that of the modified modeling secondary path component.

Thus, active noise control system controller 10 controls feedforward active noise control system 50 so that an anti-noise signal may be accurately and quickly generated by secondary source 18 to cancel or attenuate the noise signal. Active noise control system controller 10 provides both on-line feedback path modeling and on-line secondary path modeling. Feedback neutralization circuitry and secondary path compensation circuitry are also provided to eliminate or minimize any adverse effects caused by the presence of the feedback path and the secondary path to improve the overall performance of feedforward active noise control system 50. Active noise control system controller 10 allows for the cancellation of both narrowband and broadband noise signals.

FIG. 3 is a block diagram of signal discrimination circuitry 54. Although the description below and the illustration of FIG. 3 focuses on signal discrimination circuitry 54, the description and illustration of signal discrimination circuitry 54, in the one embodiment shown in FIG. 3, applies equally as well to signal discrimination circuitry 150. Of course, signal discrimination circuitry 54 and signal discrimination circuitry 150 will receive different signals and thus will generate different output signals.

Signal discrimination circuitry 54 includes a decorrelation delay unit 102, an adaptive discrimination filter 104, an adaptive algorithm 106, and a summing junction 100. Decorrelation delay unit 102 and summing junction 100 receive feedback neutralized primary signal x'(n) from summing junction 52. Decorrelation delay unit 102 is a digital delay that delays feedback neutralized primary signal x'(n) by a selected number of sampling periods. Preferably, decorrelation delay unit 102 provides a delay that is equal to or greater than the delay provided through the feedback path. For example, the time it takes for feedback signal 22 to propagate from the output of active noise control system controller 10 to the output of reference sensor 16 may be the delay provided through the feedback path. Although the delay of decorrelation delay unit 102 is preferably set at a delay that is equal to or greater than the delay of the feedback path, performance is enhanced even when a delay time as low as one sample period is provided. Thus, the present invention encompasses a delay of one sample period or more.

Adaptive discrimination filter 104 and adaptive algorithm 106 both receive the output signal from decorrelation delay unit 102. Adaptive algorithm 106 also receives modified modeling feedback signal v'(n) as an input signal and uses this as an error signal. Adaptive algorithm 106 calculates the taps or coefficients for adaptive discrimination filter 104 that will minimize the modified modeling feedback signal v'(n). In response, adaptive discrimination filter 104 receives the output of decorrelation delay unit 102 and generates predicted noise signal u(n) which, ideally, is equivalent to the actual noise signal. Thus, the modified modeling feedback component is removed and predicted noise signal u(n) is provided to summing junction 100 where it is subtracted from feedback neutralized primary signal x'(n) to generate modified modeling feedback signal v'(n) by removing the noise signal component of feedback neutralized primary signal x'(n).

Adaptive discrimination filter 104 and adaptive algorithm 106 may be implemented as any digital adaptive filter and adaptive algorithm such as those described below with reference to adaptive noise control system filter 66, adaptive active noise control filter 200, and adaptive algorithm 204. For example, adaptive discrimination filter 104 may be any type of digital filters such as an FIR or an IIR filter and adaptive algorithm 106 may be a recursive or non-recursive algorithm. Decorrelation delay unit 102 may be implemented using a computer memory or register so that the desired delay in feedback neutralized primary signal x'(n) may be provided to decorrelate the modified modeling feedback component of feedback neutralized primary signal x'(n) while leaving the narrowband components correlated. As a consequence of the delay and as desired, adaptive discrimination filter 104 will only be able to predict or generate the signal components that remain correlated.

As mentioned above, the illustration and description of signal discrimination circuitry 54 applies also to signal discrimination circuitry 150. However, a few differences should be clarified with respect to the implementation of signal discrimination circuitry 150. First, signal discrimination circuitry 150 receives the error signal e(n) from secondary source 18 and generates the modified modeling secondary output signal v"(n) as an output signal. Next, the delay provided by decorrelation delay unit 102 will, preferably, be a delay that is equal to or greater than the delay provided through the secondary path. For example, the time it takes for the modeling signal v(n) to travel through the secondary path may be the delay provided by decorrelation delay unit 102. Although the delay of decorrelation delay unit 102 is preferably set at a delay that is equal to or greater than the delay of the secondary path, performance is enhanced even when a delay time as low as one sample period is provided. Also, the modified modeling secondary output signal v"(n) is provided to adaptive algorithm 106, and adaptive discrimination filter 104 generates predicted noise signal u(n) which, ideally, is equivalent to the error signal e(n) without the modified modeling secondary path component.

FIG. 4 is a block diagram of system and secondary path adaptive filter circuitry 66 and includes adaptive active noise control system filter 200, secondary path compensation filter 202, and adaptive algorithm 204. System and secondary path adaptive filter circuitry 66 receives the processed primary signal r(n), the error signal e(n), and periodically receives filter taps or coefficients used by secondary path compensation filter 202. In response, system and secondary path adaptive filter circuitry 66 generates the generated secondary signal s(n) which is later combined with modeling signal v(n) and provided as secondary signal y(n).

Adaptive active noise control system filter 200 and secondary path compensation filter 202 receive the processed primary signal r(n) . Secondary path compensation filter 202 filters the processed primary signal, using the filter taps previously provided from on-line secondary path modeling adaptive filter 154, and generates the secondary path compensated primary signal. Secondary path compensation filter 202 is a non-adaptive digital filter that filters the processed primary signal r(n) to remove the secondary path effects from this signal.

The secondary path compensated primary signal and the error signal e(n) are provided to adaptive algorithm 204 where the coefficients or taps of adaptive active noise control system filter 200 are generated. Adaptive algorithm 204 generates the taps or coefficients that will minimize the value of error signal e(n). Adaptive active noise control system filter 200 and adaptive algorithm 204 function together to generate the generated secondary signal s(n). In response to receiving the taps from adaptive algorithm 204, adaptive active noise control system filter 200 receives processed primary signal r(n) and generates the generated secondary signal s(n) at an appropriate value to cancel the noise signal.

Adaptive active noise control system filter 200 may be implemented as any type of digital adaptive filter, such as an FIR filter or transversal filter, an IIR filter, a lattice filter, a subband filter, or virtually any other digital filter capable of performing adaptive filtering. Preferably, adaptive active noise control system filter 200 will be implemented as an FIR filter for increased stability and performance.

The adaptive algorithm used in adaptive algorithm 204 may include any known or available adaptive algorithms such as, for example, a LMS algorithm, a normalized LMS algorithm, a correlation LMS algorithm, a leaky LMS algorithm, a partial-update LMS algorithm, a variable-step-size LMS algorithm, a signed LMS algorithm, or a complex LMS algorithm. Adaptive algorithm 204 may use a recursive or a non-recursive algorithm depending on how adaptive active noise control system filter 200 is implemented. For example, if adaptive active noise control system filter 200 is implemented as an IIR filter, a recursive LMS algorithm may be used in adaptive algorithm 204. A good overview of the primary adaptive algorithms is provided in Sen M. Kuo & Dennis R. Morgan, *Active Noise Control Systems: Algorithms and DSP Implementations,* (1996). Also, the combination of secondary path compensation filter 202 and adaptive algorithm 204 may be referred to as a filtered-X LMS algorithm.

Thus, it is apparent that there has been provided, in accordance with the present invention, an active noise control system and method for on-line feedback path modeling and on-line secondary path modeling that eliminate or reduce the adverse effects of the feedback path and secondary path on overall system operation and that satisfy the advantages set forth above. Although the preferred embodiment has been described in detail, it should be understood that various changes, substitutions, and alterations can be made herein without departing from the scope of the present invention. It should also be understood that the present invention may be implemented to reduce any noise source including, but not limited to, vibrations, acoustical signals, electrical signals, and the like. The circuits and functional blocks described and illustrated in the preferred embodiment as discrete or separate circuits or functional blocks may be combined into one or split into separate circuits or functional blocks without departing from the scope of the present invention. Furthermore, the direct connections illustrated herein could be altered by one skilled in the art such that two circuits or functional blocks are merely coupled to one another through an intermediate circuit or functional block without being directly connected while still achieving the desired results demonstrated by the present invention. Also, the specified signals illustrated herein could be altered by one skilled in the art such that a signal is merely processed or summed with another signal during an intermediate step while still achieving the desired results demonstrated by the present invention. For example, the feedback neutralized primary signal may be provided to system and secondary path adaptive filter circuitry 66 with or without having the modified modeling signal v'(n) subtracted. Other examples of changes, substitutions, and alterations are readily ascertainable by one skilled in the art and could be made without departing from the spirit and scope of the present invention as defined by the following claims.

What is claimed is:

1. An active noise control system for generating an anti-noise signal to attenuate a noise signal provided through a media, the active noise control system performing on-line feedback path modeling and on-line secondary path modeling, the active noise control system comprising:

a reference sensor operable to receive the noise signal and a feedback signal and to generate a primary signal in response;

a secondary source operable to receive a secondary signal and to generate a corresponding anti-noise signal that is provided to the media to attenuate the noise signal;

an error sensor operable to receive a residual signal that is the combination of the noise signal and the anti-noise signal as received at the error sensor, and to generate an error signal in response; and an active noise control system controller operable to receive the primary signal and the error signal and to generate the secondary signal while performing on-line feedback path modeling and on-line secondary path modeling, the active noise control system controller including:

a modeling signal generator operable to generate a modeling signal, an on-line feedback path modeling adaptive filter operable to receive the modeling signal and a feedback path modeling error signal and to filter the modeling signal to generate a first output signal, the on-line feedback path modeling adaptive filter operable to generate filter taps to minimize the feedback path modeling error signal, a feedback signal discrimination circuitry operable to receive a feedback neutralized primary signal and to generate a modified modeling feedback signal, a first summing junction operable to subtract the first output signal of the on-line feedback path modeling adaptive filter from the modified modeling feedback signal to generate the feedback path modeling error signal used by the on-line feedback path modeling adaptive filter, a feedback neutralization filter operable to receive and use the filter taps generated by the on-line feedback path modeling adaptive filter and to filter a generated secondary signal to generate an anti-noise feedback component of the primary signal, a second summing junction operable to subtract the anti-noise feedback component from the primary signal to generate the feedback neutralized primary signal, an on-line secondary path modeling adaptive filter operable to receive the modeling signal and a secondary path modeling error signal and to filter the modeling signal to generate a second output signal, the on-line secondary path modeling adaptive filter operable to generate filter taps to minimize the secondary path modeling error signal, a secondary path signal discrimination circuitry operable to receive the error signal and to generate a modified modeling secondary path signal, a third summing signal junction operable to subtract the second output signal of the on-line secondary path modeling adaptive filter from the modified modeling secondary path signal to generate the secondary path modeling error signal used by the on-line secondary path modeling adaptive filter, a secondary path compensation filter operable to receive and use the filter taps generated by the on-line secondary path modeling adaptive filter and to filter the feedback neutralized primary signal to generate a secondary path compensated primary signal, a system adaptive filter operable to receive the feedback neutralized primary signal, the error signal, and the secondary path compensated primary signal and to filter the feedback neutralized primary signal to generate a generated secondary signal, and a fourth summing junction operable to combine the generated secondary signal with the modeling signal to generate the secondary signal.

2. The active noise control system of claim 1, further comprising:

a first interface circuit operable to convert the primary signal from the analog domain to the digital domain and to provide the primary signal to the active noise control system controller in the digital domain;

a second interface circuit operable to convert the secondary signal from the digital domain to the analog domain and to provide the secondary signal to the secondary source in the analog domain; and a third interface circuit operable to convert the error signal from the analog domain to the digital domain and to provide the error signal to the active noise control system controller in the digital domain.

3. The active noise control system of claim 1, wherein the primary signal includes a noise signal component, an anti-noise feedback component and a modified modeling feedback component, and the error signal includes a modified modeling secondary path component.

4. The active noise control system of claim 1, wherein the average amplitude of the modeling signal is smaller than the average amplitude of the noise signal.

5. The active noise control system of claim 1, wherein the active noise control system is a feedforward active noise control system.

6. The active noise control system of claim 1, further comprising:

a fifth summing junction operable to subtract the modified modeling feedback signal from the feedback neutralized primary signal to generate a processed primary signal, and wherein the system adaptive filter is operable to receive the processed primary signal, the error signal, and the secondary path compensated primary signal and to filter the processed primary signal to generate the generated secondary signal.

7. An active noise control system controller for receiving a primary signal and an error signal and generating a secondary signal in response, the active noise control system controller comprising:

a modeling signal generator operable to generate a modeling signal;

an on-line feedback path modeling adaptive filter operable to receive the modeling signal and a feedback path modeling error signal and to filter the modeling signal to generate a first output signal, the on-line feedback path modeling adaptive filter operable to generate filter taps to minimize the feedback path modeling error signal;

a feedback signal discrimination circuitry operable to receive a feedback neutralized primary signal and to generate a modified modeling feedback signal;

a first summing junction operable to subtract the first output signal of the on-line feedback path modeling adaptive filter from the modified modeling feedback signal to generate the feedback path modeling error signal used by the on-line feedback path modeling adaptive filter;

a feedback neutralization filter operable to receive and use the filter taps generated by the on-line feedback path modeling adaptive filter and to filter a generated secondary signal to generate an anti-noise feedback component of the primary signal;

a second summing junction operable to subtract the anti-noise feedback component from the primary signal to generate feedback neutralized primary signal;

an on-line secondary path modeling adaptive filter operable to receive the modeling signal and a secondary path modeling error signal and to filter the modeling signal to generate a second output signal, the on-line secondary path modeling adaptive filter operable to generate filter taps to minimize the secondary path modeling error signal;

a secondary path signal discrimination circuitry operable to receive the error signal and to generate a modified modeling secondary path signal;

a third summing junction operable to subtract the second output signal of the on-line secondary path modeling adaptive filter from the modified modeling secondary path signal to generate the secondary path modeling error signal used by the on-line secondary path modeling adaptive filter;

a secondary path compensation filter operable to receive and use the filter taps generated by the on-line secondary path modeling adaptive filter and to filter the feedback neutralized primary signal to generate a secondary path compensated primary signal;

a system adaptive filter operable to receive the feedback neutralized primary signal, the error signal, and the secondary path compensated primary signal and to filter the feedback neutralized primary signal to generate a generated secondary signal; and a fourth summing junction operable to combine the generated secondary signal with the modeling signal to generate the secondary signal.

8. The active noise control system controller of claim 7, further comprising:

a fifth summing junction operable to subtract the modified modeling feedback signal from the feedback neutralized primary signal to generate a processed primary signal, and wherein the system adaptive filter is operable to receive the processed primary signal, the error signal, and the secondary path compensated primary signal and to filter the processed primary signal to generate the generated secondary signal.

9. The active noise control system controller of claim 7, wherein the on-line feedback path modeling adaptive filter uses an adaptive algorithm to calculate the filter taps of the on-line feedback path modeling adaptive filter to minimize the mean-square value of the feedback path modeling error signal.

10. The active noise control system controller of claim 7, wherein the filter taps are provided to the feedback neutralization filter at desired intervals.

11. The active noise control system controller of claim 7, wherein the filter taps are provided to the secondary path compensation filter at desired intervals.

12. The active noise control system controller of claim 7, wherein the feedback signal discrimination circuitry includes:

a decorrelation delay unit operable to delay the feedback neutralized primary signal and to provide a delayed feedback neutralized primary signal;

an adaptive discrimination filter operable to receive the delayed feedback neutralized primary signal and the modified modeling feedback signal and to filter the delayed feedback neutralized primary signal to generate a predicted noise signal; and a fifth summing junction operable to subtract the predicted noise signal from the feedback neutralized primary signal to generate the modified modeling feedback signal.

13. The active noise control system controller of claim 12, wherein the decorrelation delay unit is implemented using digital circuitry.

14. The active noise control system controller of claim 13, wherein the delay of the decorrelation delay unit is a programmable delay.

15. The active noise control system controller of claim 13, wherein the delay of the decorrelation delay unit is equal to or greater than the delay of the feedback path being modeled.

16. The active noise control system controller of claim 7, wherein the modeling signal generator is a white noise generator.

17. The active noise control system controller of claim 7, wherein the system adaptive filter includes an adaptive algorithm that uses a least-means-square adaptive algorithm.

18. A method for on-line feedback path modeling and on-line secondary path modeling comprising the steps of:

receiving a primary signal;

generating a modeling signal;

s generating filter taps for use in a feedback neutralization filter using the modeling signal and a modified modeling feedback signal, generating a feedback neutralized primary signal using the feedback neutralization filter;

generating the modified modeling feedback signal using the feedback neutralized primary signal;

receiving an error signal;

generating a modified modeling secondary path signal using the error signal;

generating filter taps for use in a secondary path compensation filter using the modeling signal and the modified modeling secondary path signal;

generating a secondary path compensated primary signal using the secondary path compensation filter;

generating a generated secondary signal using the secondary path compensated primary signal and the feedback neutralized primary signal; and generating a secondary signal using the generated secondary signal and the modeling signal.

19. The method of claim 18, wherein the generating the modified modeling feedback signal step includes using a digital delay that is equal to or greater than the delay of the feedback path being modeled.

* * * * *